United States Patent
Belew et al.

(10) Patent No.: US 6,852,230 B2
(45) Date of Patent: Feb. 8, 2005

(54) METHOD FOR THE MANUFACTURE OF COMPOSITIONS CONTAINING LOW CONCENTRATIONS OF SALTS

(75) Inventors: Makonnen Belew, Uppsala (SE); Bo-Lennart Johansson, Uppsala (SE); Jean-Luc Maloisel, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 69 days.

(21) Appl. No.: 10/451,195

(22) PCT Filed: Dec. 19, 2001

(86) PCT No.: PCT/EP01/15015
§ 371 (c)(1),
(2), (4) Date: Jun. 19, 2003

(87) PCT Pub. No.: WO02/053288
PCT Pub. Date: Jul. 11, 2002

(65) Prior Publication Data
US 2004/0050784 A1 Mar. 18, 2004

(30) Foreign Application Priority Data
Dec. 31, 2000 (SE) .............................................. 0004933

(51) Int. Cl.$^7$ ............................................... B01D 15/08
(52) U.S. Cl. .................... 210/635; 210/656; 210/198.2; 530/413; 530/416; 530/417
(58) Field of Search ................................. 210/635, 656, 210/659, 660, 679, 681, 198.2; 530/413, 416, 417

(56) References Cited

U.S. PATENT DOCUMENTS

| | | | | |
|---|---|---|---|---|
| 3,234,199 A | * | 2/1966 | Reid ........................... | 530/380 |
| 4,436,656 A | * | 3/1984 | Sasaki et al. ................ | 530/322 |
| 4,599,197 A | * | 7/1986 | Wetzel ........................ | 530/405 |
| 5,652,348 A | * | 7/1997 | Burton et al. ................. | 536/20 |
| 6,245,238 B1 | * | 6/2001 | Agner ......................... | 210/635 |
| 6,310,199 B1 | * | 10/2001 | Smith et al. ................ | 536/25.4 |

FOREIGN PATENT DOCUMENTS

| | | | | |
|---|---|---|---|---|
| WO | WO 94/06822 | * | 3/1994 | ................. 210/656 |
| WO | WO96/09116 | | 3/1996 | ................. 210/656 |
| WO | WO99/65607 | | 12/1999 | ................. 210/656 |
| WO | WO00/69872 | | 11/2000 | ................. 210/656 |
| WO | WO01/38227 | | 5/2001 | ................. 210/656 |
| WO | WO02/05959 | | 1/2002 | ................. 210/656 |

* cited by examiner

Primary Examiner—Ernest G. Therkorn
(74) Attorney, Agent, or Firm—Royal N. Ronning, Jr.; Stephen G. Ryan; Yonggang Ji

(57) ABSTRACT

Method for desalting an aqueous liquid containing a charged substance comprising the steps of: (i) contacting liquid (I) with an ion-exchanger (1) under conditions permitting binding between ion-exchanger and substance, said ion-exchanger comprising a base matrix carrying an ion-exchange ligand (Ligand 1) with the opposite charge compared to the substance, (ii) desorbing said substance from said ion-exchanger by the use of a liquid (liquid (II)). Wherein: (A) ion-exchanger (1) is an ion-exchanger: (a) that can bind the substance in an aqueous reference liquid at ionic strength corresponding to 0.1 M NaCl, preferably 0.25 M NaCl; and (b) permits a breakthrough capacity at the pH provided by liquid (I) which is more than 2 mg/ml of gel, at a breakthrough of 10% and linear flow velocity of 300 cm/h; and (B) in step (ii) the pH of liquid (11) is adjusted to a pH value where the charge difference between the substance, the ligand and/or the ion-exchanger is lowered.

17 Claims, No Drawings

METHOD FOR THE MANUFACTURE OF COMPOSITIONS CONTAINING LOW CONCENTRATIONS OF SALTS

REFERENCE TO RELATED APPLICATIONS

This application is a 371 of PCT/EP01/15015 filed Dec. 19, 2001.

TECHNICAL FIELD

This invention concerns a method for the removal of salt from a liquid (I) containing a charged substance together with salt, i.e. the manufacture of desalted compositions of the substance, or desalting of the substance.

The method comprises the steps of:
(i) contacting liquid (I) with an ion-exchanger (1) under conditions permitting binding between the ion-exchanger and the substance,
(ii) desorbing said substance from said ion-exchanger by the use of a liquid (liquid (II)).

The charged substance typically is bio-organic and/or amphoteric. With respect to the number of charged groups in the substance, the greatest advantages are obtained if there are two or more charged groups, such as one, two, or more positively charged groups and/or one, two or more negatively charged groups. With respect to the molecular weight of the substances the greatest advantages are achieved if the molecular weight is above 1,000 Dalton, such as above 5,000 Dalton or above 10,000 Dalton.

A ligand is a group that is linked to the base matrix and exerts an attractive interaction with the substance of interest during the conditions provided by liquid (I). The term "ligand" includes that there is a plurality of individual ligand groups of the same kind bound to the same base matrix. At least a portion of the ion-exchange ligand on the ion-exchanger has a charge that is opposite to the charge of the substance under the conditions provided by liquid (I). The following applies for ion-exchange ligands that have a pH-dependent charge:

a) Both of the ion-exchange ligand and its corresponding base is considered being ligands of the same kind as long as pH of liquid (I) is $\leq pKa+2$.
b) Both of the ion-exchange ligand and its corresponding acid is considered being ligands of the same kind as long as the pH of liquid (I) is $\geq pKa-2$.

pKa stands for the pKa of (a) the ligand (alternative a) or the acid corresponding to the ligand (alternative b). If the pH of liquid (I) does not comply with these criteria the charged form of the ligand is present in non-essential amounts.

If not otherwise indicated, the term "charge", refers to the net charge of a substance or a ligand, respectively.

By the term "salt" in the context of the invention is meant a compound that, when dissolved in either liquid (I) or liquid (II), forms positively charged moieties and negatively charged moieties. The moiety of the salt which has the same charge as the substance to be desalted (adsorbed) is preferably non-polymeric and carries a low number of charges of the same kind as the substance (e.g. one, two or three). The other moiety of the salt does not have these restrictions although mostly salts only containing non-polymeric moieties are contemplated.

The various charged moieties of a salt may be buffering or non-buffering.

BACKGROUND

Desalted compositions of charged bio-organic substances are needed in many cases where a bio-organic substance is to be further processed. Traditional ion-exchange chromatography, fore instance, requires that the ionic strength of the solution from which a substance is to be adsorbed must have an ionic strength below a particular value that depends on the substance, other ions present, ion-exchanger to be used etc. Analytical methods used for bio-organic substances may be disturbed by the presence of salts leading to inaccurate results. Typical examples are mass spectrometry, elemental analyses, etc. Desalting is often an important process in the manufacturing of bio-organic substances of pharmaceutically acceptable purity and/or of purity acceptable for the food industry.

Conventional desalting procedures for bio-organic substances have been gel filtration, membrane filtration, ultrafiltration, dialysis etc. It has also been suggested to use (a) ion-exchangers in combination with a pH-switch for the desorption of the bio-organic substance in order to reduce the charge interaction the adsorbed substance and the ion-exchanger, and (b) strong ammonium ion-exchangers in combination with desorption with volatile buffers. See for instance Hirs et al., J. Biol. Chem 195 (1952) 669–683 and 219 (1956) 623–642; Hirs, Methods in Enzymology XI (ed. Hirs) (1967) 386–390; Dréze et al., and Analytica Chim Acta 11 (1954) 554–558, which are describing desalting of amino acids and short peptides. See also WO 9406822 (Upfront Chromatography) and WO 9965607 (Amersham Pharmacia Biotech AB) that suggest desalting of proteins.

U.S. Pat. No. 5,652,348 (Burton et al) suggests that by utilising chargeable ligands under hydrophobic interaction conditions desorption can be accomplished without salting or desalting. Hydrophobic interaction conditions mean that the ligand is in uncharged form and that the concentration of salt is high.

THE OBJECTIVES OF THE INVENTION

One main objective is to provide a simple and reliable desalting method of the kind given under the heading "Technical Field" in which at least one of the following features are present when going from step (i) to step (ii):

(a) simplicity, scalability to various formats (e.g. to a micro-format), reproducibility etc;
(b) mild conditions such that the primary, secondary, tertiary and/or quaternary structure of the bio-organic substance can be maintained essentially unchanged;
(c) reduction of the total concentration of salt by a factor of at least 10, preferably at least 100 (molar/molar), for instance by starting from a total concentration of salt in liquid (I) that is at least 0.1 M, such as at least 0.25 M or at least 0.5 M and going down to a total concentration of salt that is at most 0.1 M, such as at most 0.05 M or at most 0.01 M in the eluate from step (ii) containing the major part of the desorbed substance.
(d) increasing the concentration of the bio-organic substance with a factor of at least 10, such as at least $10^2$, or at least $10^3$ or more;
(e) reduction of the concentration of non-buffering salt components to be essentially zero (except for counter-ions to buffering components that are needed to maintain electrostatic balance);
(f) reduction of the amount of other bio-organic compounds, e.g. of the same general structure, with a factor of at least 10 such as at least 100 (w/w);
(g) a yield of the bio-organic substance of interest of at most 60% such as at most 75% or at least 80% or at least 90%, with preference for essentially 100%.

A second objective is to provide desalting procedures assisting in obtaining bio-organic compounds of pharmaceutically acceptable purity and/or purities acceptable for the food industry.

A third objective is to provide a desalting process for a bio-organic compound that is to be analysed as such as discussed above, i.e. analytical methods intended for bio-organic compounds of the above-mentioned kind comprising a desalting step.

A fourth objective is to provide new desalting procedures that can be used on compositions containing a charged substance as described herein prior to (a) reverse-phase chromatography, and/or (b) ion-exchange chromatography on conventional ion-exchangers by the aid of desorption by an increase in the concentration of salt, for instance a change taking place within the interval 0–0.5 M of salt, for instance in a part of the subintervals 0–0.1, 0.075–0.15 and/or 0.125–0.5 M salt, with preference for the change taking place as a step-wise or continuous gradient.

This objective also comprises the corresponding batch-wise procedures. A used salt gradient may extend up to 2–3 M salt. By conventional ion-exchangers are meant ion-exchangers that have a breakthrough capacity below the breakthrough capacity required for the ion-exchangers used in the present innovative desalting procedure. See below.

The Invention

The present inventors have discovered that the above-mentioned objectives at least partially can be complied with if an ion-exchanger is selected that has a sufficiently high breakthrough capacity at a sufficiently high ionic strength at the pH used for the adsorption step (step (i)).

One of the characteristics of the present innovative method is that it contains one or both of two key features (A and B, respectively):

Feature A: Ion-exchanger (1) is selected among ion-exchangers that:

(a) are capable of binding the substance of interest in an aqueous reference liquid at an ionic strength corresponding to 0.1 M NaCl, preferably 0.25 M NaCl; and (b) permit a breakthrough capacity at the pH provided by liquid (I) which is more than 2 mg/ml of gel (sedimented), such as more than 4 mg/ml of gel, at a breakthrough of 10% and a linear flow velocity of 300 cm/h.

Feature B. Step (ii) comprises that the pH of liquid (II) is adjusted to a pH value that means that the charge difference between the substance and the ligand and/or the ion-exchanger is lowered. Preferably the adjustment leads to a zero charge on the substance and/or on the ligand/ion-exchanger or to a charge of the same kind for both of them (either negative or positive).

An alternative selection criteria in item (b) of Feature B is that the ion-exchanger is selected among those that permit a maximal breakthrough capacity in the pH interval 2–12 for the substance which is $\geq 100\%$, such as $\geq 125\%$ or $\geq 200\%$ or $\geq 300\%$ or $\geq 500\%$ or $\geq 1000\%$, of the breakthrough capacity of the substance for the corresponding ion-exchanger in which the ion-exchange ligands are (i) SP groups when the substance has a positive charge (reference ion-exchanger 2a), and (ii) Q groups when the substance has a negative charge (reference ion-exchanger 2b);

By the term "SP groups" is meant sulphopropyl groups that can be obtained by reacting an allyl group with bisulphite, i.e. SP groups include $—CH_2CH_2CH_2SO_3^-$ and its sulphonic acid isomers.

By the term "Q groups" is meant quaternary ammonium groups that can be obtained by reacting $—OCH_2CH(OH)CH_2OCH_2CH=CH_2$ with halogen followed by reaction with trimethylamine, i.e. Q-groups include $—OCH_2CH(OH)CH_2OCH_2CH(OH)CH_2N+(CH_3)_3$ and its isomers containing a quaternary trimethylammonium group.

The comparisons above refer to measurements performed under essentially the same conditions for ion-exchanger (1) and (2a) and for ion-exchanger (1) and (2b), i.e. pH, temperature, solvent composition, flow velocity etc are the same between (1) and (2a) and between (1) and (2b). The breakthrough capacities are measured at the same relative concentration of the substance in the flow through (for instance $c/c_0=10\%$, for $c/c_0$ see the experimental part).

The "corresponding ion-exchanger" means that the support matrix is the same, i.e. support material, bead size, pore sizes, pore volume, packing procedure etc are the same. The total degree of substitution for charged ligand(s) of ion-exchanger 1 is/are essentially the same as on the reference ion-exchanger (2a or 2b) (measured as chloride and sodium ion capacity, respectively). The counter-ion should also be the same. The spacer and coupling chemistry may differ. Certain kinds of coupling chemistries may lead to cross-linking of the support matrix resulting in a more rigid matrix. In this case the flow conditions at which the comparison is made is selected at a level where the matrix is essentially non-compressed.

Typically a useful breakthrough capacity for the substance is higher than the maximal breakthrough capacity the substance has on (a) the commercially available anion-exchanger Q-Sepharose Fast Flow (Amersham Pharmacia Biotech, Uppsala, Sweden) which has a chloride ion capacity of 0.18–0.25 mmol/ml gel and/or (b) the commercially available anion-exchanger SP-Sepharose Fast Flow (Amersham Pharmacia Biotech, Uppsala, Sweden) which has a sodium ion capacity of 0.18–0.25 mmol/ml gel.

The base matrix in these two reference ion-exchangers is epichlorohydrin cross-linked agarose in beaded form. The beads have diameters in the interval 45–165 $\mu$m. The exclusion limit for globular proteins is $4 \times 10^6$.

All breakthrough capacities refer to measurements made at room temperature (about 25°).

The lowering of the charge difference in step (ii) may be accomplished by changing the net charge of the substance. If the ligand have a pH-dependent charge, the change may also involve a change of the charge of the ligand. The ligand have to be amphoteric if one wants to switch to an opposite kind of charge on the ligand, for instance in order to accomplish the same kind of charge on the substance and on the ligand.

The Ligand

The ion-exchange ligand may be an anion or a cation-exchange ligand. The ligand may contain both kinds of charge as long as the net charge is negative for a cation-exchange ligand and positive for an anion-exchange ligand.

Anion-exchange ligands typically comprise a charged group selected amongst:

(a) ammonium group, such as primary ammonium, secondary ammonium, tertiary ammonium, quaternary ammonium, and amidinium group; and (b) sulphonium.

Heteroaromatic groups in which there is a nitrogen atom in the aromatic ring are included in the term "tertiary ammonium" groups. In the same fashion, N-alkylated forms of such heteroaromatic groups are included in "quaternary ammonium" groups.

Cation-exchange ligands typically comprise a charged group selected amongst (c) carboxylate (—COO$^-$), phosphonate or phosphate (—PO$_3^{2-}$, —P(OH)O$_2^-$, and —OP(OH)O$_2^-$, —OPO$_3^{2-}$ respectively), sulphonate or sulphate (—SO$_3^-$ and —OSO$_3^-$ respectively), -aryl-O$^-$ (phenolate/arylolate) etc.

The free bond (valence) binds directly to a carbon that is part of a chain attaching the group the base matrix.

It has recently been found that ion-exchange ligands that are of the mixed mode or bimodal kind may give extremely high break-through capacities at relatively high ionic strength. See our copending International Patent Applications PCT/EP00/11605 (Amersham Pharmacia Biotech AB) and PCT/EP00/11606 (Amersham Pharmacia Biotech AB) (both anion-exchange ligands), and SE 0002688-0 filed Jul. 17, 2000 (cation-exchange ligands). See also our copending SE application "A method for mixed mode adsorption and mixed mode adsorbents" that focuses on so-called stochastic ion exchangers and has been filed in parallel with this application. These applications are hereby incorporated by reference.

By the terms "a mixed mode ligand" and "a bimodal ligand" are meant that a ligand is capable of providing at least two different, but co-operative, sites which interact with the substance to be bound. The sites are different with respect to functionality and/or kind.

Typical mixed mode ion-exchange ligands have one, two, three, four or more atoms or groups that are capable of participating in attractive interactions with the substance to be adsorbed to the ion-exchanger in step (i). These atoms or groups preferentially are located at most at a distance of 7 atoms from the charged atom or group. Hydrophobic interactions and electron-donor acceptor interactions are examples of attractive interactions.

Pure hydrophobic interaction is typically between a hydrocarbon structure in the ligand and hydrophobic regions in the substance. Typical hydrophobic structures comprise an aromatic structure and/or two, three, four or more sp-, sp$^2$- and/or sp$^3$-hybridised carbon atoms linked together. In the latter variant each carbon atom binds to another carbon atom and possibly also to one or more hydrogen atoms. Thus the preferred structures of this kind are pure alkyl groups, pure alkenyl groups, pure aryl, pure aralkyl, pure alkylaryl groups, pure alkenyl groups etc comprising 2, 3, 4, 5, 6 or more carbon atoms, and corresponding groups having two or more free bonds (valencies).

Electron-donor acceptor interactions typically require an electron acceptor atom or group in the ligand and an electron donor atom or group in the substance, or vice versa. This kind of interaction includes hydrogen-bonding, π—π, charge transfer, etc. See Karger et al., "An Introduction into Separation Science", John Wiley & Sons (1973) page 42 for a discussion about electron donor acceptor interactions.

Illustrative examples of electron donor atoms/groups are:

(a) oxygen with a free pair of electrons, such as in hydroxy, ethers, carbonyls, and esters (—O— and —CO—O—) and amides, (b) sulphur with a free electron pair, such as in thioethers (—S—), (c) nitrogen with a free pair of electron, such as in cyano, amines, amides including sulphone amides, carbamides, carbamates, amidines, etc, (d) halo (fluorine, chlorine, bromine and iodine), and (e) sp- and sp$^2$-hybridised carbons.

Typical electron acceptor atoms/groups are electron deficient atoms or groups, such as metal ions, cyano, nitrogen in nitro etc, and include also a hydrogen bound to an electronegative atom such as HO— in hydroxy and carboxy, —NH— in amides and amines, HS— in thiol etc.

Atoms or groups that participate in mixed mode interaction with the substance to be adsorbed may be present in the chain linking the charged atom or group to the base matrix, a branch attached to said chain or a separate substituent directly attached to the charged atom or group (in particular for anion-exchange groups/ligands).

An electron donor/acceptor atom or group may be present in a branch attached to the chain linking the ligand to the base matrix and at a distance of 7 or more atoms from the charged atom or charged group. In such a case the complete branch is considered as a separate ligand.

Particularly interesting mixed mode charged ligands have a thioether (—S—) and/or a sp$^2$-hybridised carbon, such as an aromatic carbon, within the above-mentioned distances of the charged atoms or groups. See for instance our copending International Patent Applications PCT/EP00/11605 (Amersham Pharmacia Biotech AB) and PCT/EP00/11606 (Amersham Pharmacia Biotech AB) (both of which refer to anion-exchange ligands), and SE 0002688-0 filed Jul. 17, 2000 (cation-exchange ligands) and WO 996507 (Amersham Pharmacia Biotech AB) (cation-exchange ligands). WO 9729825 (U.S. Pat. No. 6,090,288) (Amersham Pharmacia Biotech AB) discloses mixed mode anion-exchange ligands which have one or more hydroxy and/or amino/ammonium nitrogen at a position 2–3 carbon from a primary, secondary or tertiary ammonium nitrogen. Mixed mode ion-exchange ligands that are potentially useful in the instant innovative method are described in WO 9808603 (Upfront Chromatography), WO 9600735, WO 9609116 and U.S. Pat. No. 5,652,348 (Burton et al). All the publications referred to in this paragraph are incorporated by reference.

In the thioethers (—S—) contemplated above, each of the free bonds (valences) binds to a sp$^2$- or sp$^3$-hybridised carbon which may or may not be part of a cyclic structure that may or may not be aromatic or non-aromatic. The term "thioethers" as contemplated herein thus comprises thiophene and other heteroaromatic rings comprising sulphur as a ring atom.

The aromatic ring structure contemplated above may comprise one or more aromatic rings, for instance a phenyl, a biphenyl or a naphthyl structure and other aromatic ring systems that comprise single rings, fused rings and/or bicyclic structures. Aromatic rings may be heterocyclic, i.e. contain one or more nitrogen, oxygen or sulphur atoms, and may have substituents. Substituents may contain a pure hydrocarbon group as discussed above and/or an electron donor or acceptor atom or group, for instance enabling hydrogen-bonding and/or other electron donor-acceptor interactions. Illustrative aromatic ring structures are: hydoxyphenyl (2-, 3- and 4-), 2-benzimadozolyl, methylthioxyphenyl (2-, 3- and 4-), 3-indolyl, 2-hydroxy-5-nitrophenyl, aminophenyl (2-, 3- and 4-), 4-(2-aminoethyl)phenyl, 3,4-dihydroxyphenyl, 4-nitrophenyl, 3-trifluoromethylphenyl, 4-imidazolyl, 4-aminopyridine, 6-aminopyrimidyl, 2-thienyl, 2,4,5-triaminophenyl, 4-aminotriazinyl-, 4-sulphoneamidophenyl etc.

The pKa of the preferred anion-exchange ligands and of the corresponding acids for the preferred cation-exchange ligands can be found in the interval from 3 and upwards and is preferably below 11, preferably in the interval of 4–9 in order to permit appropriate decharging of the ion-exchange ligand.

Particularly interesting anion-exchange ligands have a pH dependent charge and have pKa values that are $\leq 12.0$, such as $\leq 10.5$. This means that these ligands comprise a charged group, which preferably is selected amongst primary or secondary ammonium groups or tertiary ammonium groups. Tertiary ammonium groups in which the nitrogen is part of an aromatic structure and ammonium groups having an aromatic carbon in its $\alpha$- or $\beta$-position may have pKa values below 8. Normally the pKa of anion-exchange ligands is $\geq 3$, such as $\geq 4$.

Particularly interesting negatively charged ligands carry a pH-dependent charge. The pka-values for the corresponding acids normally are $\geq 3$, such as $\geq 4$. These kind of ligands thus should comprise charged groups selected amongst carboxylate ($-COO^-$), phosphonate or phosphate ($-PO_3^{2-}$, $-P(OH)O_2^-$, and $-OP(OH)O_2^-$, $-OPO_3^{2-}$ respectively), -aryl-$O^-$ (phenolate/aryloate) and other weak acid groups.

This does not exclude that ion-exchanging ligands corresponding to
strong acids (pKa$\leq 3$, such as $\leq 2$ or $\leq 0$) (the corresponding base acts as a cation-exchange ligand), and
weak acids (pKa$\geq 10$, such as $\geq 12$, etc) or ligands carrying a charge that is independent of pH
will also have advantages when they are incorporated in an ion-exchanger that is to be used in our new and innovative desalting method. As for the other ion-exchanging groups, these advantages are dependent on the properties of the particular substance to be desalted, for instance its isoelectric point and the strength of its interaction with the ion-exchanger.

The pka-value of a ligand is taken as the pH at which 50% of the ligand in question are titrated.

Stochastic Ion-exchangers

Suitable ion-exchangers to be used in the inventive method may also contain two or more different ligands (Ligand 1, Ligand 2 etc). In this case at least one of the ligands (Ligand 1) is an ion-exchange ligand which is different from the other ligands (Ligand 2, for instance). This kind of ion-exchangers is called stochastic and is thoroughly described in SE application entitled "A method for mixed mode adsorption and mixed mode adsorbents" filed in parallel with this application. This SE application is hereby incorporated by reference.

Ligand 1 may have structural parts of the same kind as discussed above for ion-exchange ligands in general. Ligand 1 may or may not have a pH-dependent charge as discussed above.

Ligand 2 may be an ion-exchange ligand or a ligand that solely interacts by hydrophobic interaction and/or electron donor-acceptor interaction with the substance to be desalted. If charged, Ligand 2 may have the same or the opposite kind of charge as Ligand 1.

Ligand 1 and Ligand 2 may differ with respect to the presence and the combination of atoms or groups that give hydrophobic and/or electron donor-acceptor interactions with the substance to be adsorbed. See above.

Ligand 2 may be uncharged at the conditions provided by liquid (I). There are mainly two kinds of uncharged ligands:
(a) ligands that can be charged by a pH-switch (class I) and
(b) ligands that can not be charged by a pH-switch (class II).

Class I comprises uncharged forms of ligands that can have a pH-dependent charge. See above.

A Class II ligand contains one or more structural elements that can give rise to hydrophobic interactions and electron donor-acceptor interactions as discussed above. In a typical class II ligand there are two, three, four or more electron donor-acceptor atoms or groups as defined above. Each of the atoms or groups is separated from other electron donor acceptor atoms or groups by two, three, four or more $sp^3$-hybridised carbon atoms linked directly to each other.

A ligand of class II is defined as the outermost part of a group that is projecting from the base matrix and complies with the definition in the preceding paragraph. By the term "outermost" is contemplated atoms that are at 1–7 atoms' distance from the outermost atom that is capable of participating in electron donor-acceptor interactions or in hydrophobic interactions involving an alkyl group as defined above.

Each ligands of the second category can thus be used as Ligand 2 in the ion-exchangers provided the ligand comprises one or more atoms which enables electron donor-acceptor interactions and/or hydrophobic interactions. Examples of atoms and/or groups that may be present are: aryls that may be substituted or unsubstituted including phenyl groups, pure alkyl and pure alkylene ($C_3$ and higher with preference for less than $C_8$), thioether, ether, uncharged amino, hydroxy, amido (carboxamido including sulphonamido, carbamido, carbamate etc), nitro, sulphone, uncharged carboxy etc. In this kind of ligands, two or more $sp^3$-hybridised carbon atoms linked directly together often separate the atoms or groups from each other.

The different ligands in stochastic ion-exchangers may be present more or less at random in relation to each other in the support matrix or in a part thereof. Depending on the method of introduction the ratio between the amounts of the ligands may vary but should always be 0.01–100, with preference for 0.02–50, for at least two ligands in a substantial part of the matrix. In order to accomplish uneven or layered distribution of different ligands within a support, the general principals outlined in WO 9839364 (Amersham Pharmacia Biotech AB) can be used. Due care has to be taken with respect to reactivities, diffusivities and concentrations of ligand-forming reagents so that the sharp layers that are the primary goal in these two patent publications are not introduced. WO 9839364 is hereby incorporated by reference.

In stochastic ion-exchangers the following apply
Ligands that are introduced by the use of the same reagent and conditions, for instance in parallel during the same conditions, are considered to be of the same kind even if they are structurally different. This in particular applies if different isomers are introduced at the same time.
Ligands that are residual groups (unreacted groups) even after the use of large excesses of derivatising reagents in order to minimise their presence are considered non-existent. Typically residual groups are present in molar amounts less than 10% such as less than 5% compared to the starting amount of the group to be derivatized.

Particularly interesting stochastic ion exchangers comprise as Ligand 1 a strong ion-exchange ligand and as Ligand 2 a ligand can be charged/decharged by a switch in pH. Two typical combinations are:
(a) a strong cation-exchange ligand as Ligand 1 combined with a weak anion-exchange ligand as Ligand 2, or
(b) a strong anion-exchange ligand as Ligand 1 and a weak cation-exchange ligand as Ligand 2.

In this context a strong cation-exchange ligand has a corresponding acid with a pKa<3–4. Examples of strong anion-exchange ligands are quaternary ammonium ligands and anion-exchange ligands having a pKa>10, such as ≧11 or ≧12. Other kinds of ion-exchange ligands are considered weak.

Other interesting combinations are for instance stochastic ion-exchangers having two different weak anion- or cation-exchange ligands of similar pKa on the same base matrix, or a weak anion- and a weak cation-exchange ligand bound to the same matrix. The ligands can be selected such that the difference in pKas is less than, larger than or equal to two, three or four pH-units.

The largest advantages with combining ligands of different kind concern desalting of amphoteric substances. The ligands are typically combined in such a way that one of the ligands is charged (Ligand 1) while the other one (Ligand 2) is uncharged during step (i) and capable of becoming charged with the same charge as the substance to be released during step (ii). It follows that the proper combination will depend on the isoelectric point (pI) of the substance to be desalted. See further below.

Support Matrix/Base Matrix

The support matrix comprises the base matrix and any spacer attaching a ligand to the base matrix.

The base matrix is based on organic and/or inorganic material.

The base matrix is preferably hydrophilic and in the form of a polymer, which is insoluble and more or less swellable in water. Hydrophobic polymers that have been derivatized to become hydrophilic are included in this definition. Suitable polymers are polyhydroxy polymers, e.g. based on polysaccharides, such as agarose, dextran, cellulose, starch, pullulan, etc. and completely synthetic polymers, such as polyacrylic amide, polymethacrylic amide, poly(hydroxyalkylvinyl ethers), poly(hydroxyalkylacrylates) and polymethacrylates (e.g. polyglycidylmethacrylate), polyvinylalcohols and polymers based on styrenes and divinylbenzenes, and copolymers in which two or more of the monomers corresponding to the above-mentioned polymers are included. Polymers, which are soluble in water, may be derivatized to become insoluble, e.g. by cross-linking and by coupling to an insoluble body via adsorption or covalent binding. Hydrophilic groups can be introduced on hydrophobic polymers (e.g. on copolymers of monovinyl and divinylbenzenes) by polymerisation of monomers exhibiting groups which can be converted to OH, or by hydrophilisation of the final polymer, e.g. by adsorption of suitable compounds, such as hydrophilic polymers.

Suitable inorganic materials to be used in base matrices are silica, zirconium oxide, graphite, tantalum oxide etc.

Preferred matrices lack groups that are unstable against hydrolysis, such as silan, ester, amide groups and groups present in silica as such. This in particular applies with respect to groups that are in direct contact with the liquids used.

The matrix may be porous or non-porous. This means that the matrix may be fully or partially permeable (porous) or completely impermeable to the substance to be removed (non-porous), i.e. the matrix should have a Kav in the interval of 0.40–0.95 for substances to be removed. This does not exclude that Kav may be lower, for instance down to 0.10 or even lower for certain matrices, for instance having extenders. See for instance WO 9833572 (Amersham Pharmacia Biotech AB).

In a particularly interesting embodiment of the present invention, the matrix is in the form of irregular or spherical particles with sizes in the range of 1–1000 $\mu$m, preferably 5–50 $\mu$m for high performance applications and 50–300 $\mu$m for preparative purposes.

Alternatively the matrix may be monolithic, such as in the form of a tube or some other kind of vessel, a porous plug, a porous membrane or a filter.

The matrix may be in form of beads/particles with a density, which is larger than the liquid used in step (i). This kind of matrices is especially applicable in large-scale operations for fluidised or expanded bed chromatography as well as for different batch wise procedures, e.g. in stirred tanks. Fluidised and expanded bed procedures are described in WO 9218237 (Amersham Pharmacia Biotech AB) and WO 9200799 (Kem-En-Tek).

The term hydrophilic matrix means that the accessible surface of the matrix is hydrophilic in the sense that aqueous liquids are able to penetrate the matrix. Typically the accessible surfaces on a hydrophilic base matrix expose a plurality of polar groups for instance comprising oxygen and/or nitrogen atoms. Examples of such polar groups are hydroxyl, amino, carboxy, ester, ether of lower alkyls (such as (—CH$_2$CH$_2$O—)$_n$H where n is an integer).

The spacer starts at the base matrix and extends to the ligand as defined above.

The spacer as such is conventional as in traditional ion-exchangers and may thus comprise linear, branched, cyclic saturated, unsaturated and aromatic hydrocarbon groups (e.g. with up to 1–20, such as 1–10 carbon atoms) as discussed above. These groups may comprise pure hydrocarbon groups of the type discussed above, hydroxy groups, alkoxy and aryloxy and the corresponding thio analogues, and/or amino groups. Carbon chains in hydrocarbon groups may at one or more positions be interrupted by ether oxygen and thioether sulphur. There may also be carbonyl groups, such as in amide and ketone groups, and other groups having the comparable stability against hydrolysis. At most one atom selected from oxygen, sulphur and nitrogen is preferably bound to one and the same sp$^3$-hybridised carbon atom.

It is apparent that the spacer may provide one or more electron donor or acceptor atoms or groups enhancing binding of the desired substance to the ion-exchanger as discussed above, for instance by participating in hydrogen-bonding. For reason of simplicity, this kind of atoms or groups is considered part of the spacer. There may also be attached more than one ligand to one and the same spacers. See "branches" above.

Ligand Density

The level of the ion-exchange ligands of the adsorbents used in the invention is usually selected in the interval of 0.001–4 mmol/mL of the matrix, such as 0.002–0.5 mmol/mL of the matrix, with preference for 0.005–0.3 mmol/mL of the matrix. Preferred ranges are among others determined by the kind of matrix, kind of ligand, substance to be adsorbed etc. The expression "mmol per mL of the matrix" refers to fully sedimented matrices saturated with water. The ligand density range refers to the capacity of the matrix in fully protonated/charged form to bind common counterions such as sodium ions and/or chloride ions and depends on the kind of anionic and/or cationic ligands that is present, among others.

Best Mode

The best mode variants of the invention vary with the substance of interest. The best modes so far discovered are presented in the experimental part.

Adsorption/desorption

The adsorption and/or desorption steps (step (i) and step (ii)) may be carried out as a chromatographic procedure with the ion-exchange matrix in a monolithic form or as particles in the form of a packed or a fluidised bed. For particulate matrices, these steps may also be carried out in a batch-wise mode with the particles being more or less completely dispersed in the liquid.

The liquids used in steps (i) and (ii) are aqueous, i.e. water, possibly mixed with a water-miscible solvent.

Adsorption (Step (i))

During adsorption, a liquid sample containing the charged substance is contacted with the ion-exchanger defined above under conditions permitting adsorption (binding), e.g. by ion-exchange. In other words the substance carries at least one group or atom that is oppositely charged compared to the ion-exchange ligand/ion-exchanger.

Preferably the net charge of the substance is opposite to the net charge of the ion-exchanger during step (i). For an amphoteric substance this means that the pH for anion-exchange conditions is $\geq pI-0.5$, preferably $\geq pI$, and for cation-exchange conditions $\leq pI+0.5$, preferably $\leq pI$.

One of the benefits of the invention is that it will be possible to carry out adsorption/binding also at elevated ionic strengths compared to what normally has been done for conventional ion-exchangers (e.g. the reference anion-exchangers as defined above). In absolute figures this means that adsorption according to the present invention may be performed at ionic strengths above or below 15 or 20 mS/cm. The ionic strength may exceed 30 mS/cm and in some cases even exceed 40 mS/cm. Useful ionic strengths often correspond to NaCl concentrations (pure water) $\geq 0.1$ M, such as $\geq 0.3$ M or even $\geq 0.5$ M. The conductivity/ionic strengths to be used will depend on the ligands combined, their densities on the matrix, the substance to be bound and its concentration etc.

Desorption (Step (ii))

The desorption process, i.e. the replacement of liquid (I) for liquid (II) comprises changing the pH in order to weaken the interaction between the desired substance and the ligands. At the same time the ionic strength or salt concentration is diminished, preferably to a level such that the only salt present are the buffering components and if needed also their non-buffering counterions.

Weakening of the interaction by a change in pH includes (a) diminishing the charge of ligands that bind via ion-ion attractive interaction to the desired substance, and/or (b) diminishing the charge of a group on the desired substance that binds to a ligand having the opposite charge. The pH-change can many times be taken so far that the ligand and the substance to be desalted will have the same charge during step (ii).

The change in pH in step (ii) means that a significantly lowered ionic strength will be required compared to the ionic strength of liquid (I) in step (i). The substance can thus be eluted in concentrated form in a solution of low concentration of salt, e.g $\leq 100$ mM or even $\leq 10$ mM. The concentration factor may be of the same size as given under objectives of the invention.

In case the adsorption step has been performed under anion-exchange conditions, the appropriate pH in step (ii) is below pI+2 or below pI+1, with preference for pH$\leq$pI.

In case the adsorption step has been under cation-exchange condition, the appropriate pH in step (ii) shall be above pI−2 or above pI−1, with preference for pH$\geq$pI.

The term pI in the preceding two paragraphs refers to the pI of the substance to be desorbed (desalted).

Typical salts to be used for changing the ionic strength are selected among chlorides, phosphates, sulphates etc of alkali metals or ammonium ions).

Typical buffer components to be used for changing pH are depending on the kind of ligands involved. For instance, if the ion-exchange ligand is cationic the buffering acid base pair is preferably selected amongst acid-base pairs in which the buffering components can not bind to the ligand, i.e. buffers based on piperazine, 1,3-diaminopropane, ethanolamine etc. In the analogous fashion the buffering acid-base pair in the case the ion-exchange ligand is anionic is phosphate, citrate, acetate, etc.

The preferred buffering acid-base pairs contains at least one buffering component that (the acid or the base) which is volatile and/or uncharged. This will mean that the buffer components can be removed simply by evaporation after step (ii). Volatile buffer components typically have a vapour pressure that is $\geq 1$ mm Hg, such as $\geq 10$ mm Hg, at 25° C.

Desorption may be assisted by adjusting the polarity of liquid (II) to a value lower than the polarity of the adsorption liquid (I). This may be accomplished by including a water-miscible and/or less hydrophilic organic solvent in liquid II. Examples of such solvents are acetone, methanol, ethanol, propanols, butanols, dimethyl sulfoxide, dimethyl formamide, acrylonitrile etc. A decrease in polarity of liquid II (compared to aqueous liquid I) is likely to assist in desorption and thus also reduce the ionic strength needed for release of the substance from the matrix. Preferably the organic solvent is volatile with a vapour pressure $\geq 1$ mm Hg, such as $\geq 10$ mm Hg, at 25° C.

Desorption may also be assisted by including a soluble structural analogue of one or more of the ligands used. The concentration of a structural analogue in liquid (II) should be larger than its concentration in aqueous liquid (I). A "structural analogue of the ligand" or a "ligand analogue" is a substance that has a structural similarity with the ligand and in soluble form is capable of inhibiting binding between the ligand and the substance to be removed. Structural ligand analogues when used for desorption should be neutral and preferably volatile as defined for an organic solvent.

Desorption by a pH-change may also be assisted by an increase in ionic strength (addition of salt) provided it does exceed half of the ionic strength of liquid (I).

The change from liquid (I) to liquid (II) can be accomplished in one or more steps (step-wise gradient) or continuously (continuous gradient). The various variables of the liquid in contact with the matrix may be changed one by one or in combination. This means that the desired substance many times can be eluted free from other adsorbed substances that elute at other pH-values and/or ionic strengths.

Important Variants Utilising Stochastic Ion-exchangers

Variant 1: Ligand 1 is a cation-exchange ligand that has a pH-dependent negative charge and ligand 2 is either unchargeable or a chargeable base for which a significant portion is uncharged at the pH of step (i). pKa of the acid corresponding to ligand 1 is lower than pKa of the acid corresponding to ligand 2 (if chargeable). The substance to be adsorbed has a pI, which is above pKa of ligand 2. The pH of liquid (I) is selected such that the substance has a net positive charge, i.e. will adsorb to the ion-exchanger. By decreasing the pH, the substance and possibly also ligand 2 will be protonated and receive an increased positive charge. This will assist the release of the substance at a moderate pH and will permit desorption at a lowered salt concentration in liquid (II).

Variant 2: Ligand 1 comprises an anion-exchange ligand that has a pH dependent positive charge and ligand 2 is either completely unchargeable or a chargeable acid form for which a significant portion is uncharged at the pH of the step (i). The pKa of the ligand 2 is higher than the pKa of the ligand 1. The pI of the substance to be adsorbed (desalted) is below both pKa of ligand 1 and pKa of ligand 2. The pH of liquid (I) (step (i)) is such that substance has a net negative charge and ligand 1 a positive charge while ligand 2 is essentially uncharged. The substance thus will be adsorbed in step (i). By increasing the pH, ligand 2 will become negatively charged meaning desorption of the substance at a lowered salt concentration in liquid (II).

Recovery

The present inventive desalting method enables high recoveries of an adsorbed substance, for instance recoveries above 60% such as above 80% or above 90% (step (i) to step (ii)). The recovery can exceed 95% or be essentially quantitative. Typically the amount of the substance applied to the ion-exchanger is in the interval of 10–80%, such as 20–60%, of the total binding capacity of the ion-exchanger for the substance.

The Substance to be Removed from the Liquid (I)

The present invention is primarily intended for large molecular weight substances that have several structural units that can interact with the ligands defined above. Appropriate substances have a molecular weight that is above 1000 Dalton, and is bio-organic and polymeric. The number of charged groups per molecule is typically one or more and depends upon pH. Further comments concerning the molecular weight and the number of charges are given under the heading "Technical Field". The substances may be amphoteric. The substances typically comprise a structure selected amongst peptide structure (for instance oligo- or polypeptide structure), nucleic acid structure, carbohydrate structure, lipid structure, steroid structure, amino acid structure, nucleotide structure and any other bio-organic structure that is charged or can be charged by a pH-switch.

The substance may be dissolved in the aqueous medium or be in the form of small bio-particles, for instance of colloidal dimensions. Illustrative examples of bio-particles are viruses, cells (including bacteria and other unicellular organisms) and cell aggregates and parts of cells including cell organelles.

It is believed that the invention in particular will be applicable to aqueous liquids that are derived from biological fluids comprising a substance of interest together with high concentrations of salts.

Typical liquids of high ionic strength that contain bio-organic substances of the kind discussed above are fermentation broths/liquids, for instance from the culturing of cells, and liquids derived therefrom. The cells may originate from a vertebrate, such as a mammal, or an invertebrate (for instance cultured insect cells such as cells from butterflies and/or their larvae), or a microbe (e.g. cultured fungi, bacteria, yeast etc). Included are also plant cells and other kinds of living cells, preferably cultured.

In the case liquid (I) also contains undesirable particulate matter then it may be beneficial to utilise expanded bed technology. This particularly applies when liquid (I) originates from (a) a fermentation broth/liquid from the culture of cells, (b) a liquid containing lysed cells, (c) a liquid containing cell and/or tissue homogenates, and (d) pastes obtained from cells.

The innovative desalting procedure now described can be used as given in the $2^{nd}$–$4^{th}$ objectives.

The invention will now be illustrated with patent examples. The invention is further defined in the appending claims.

Experimental Part

1. Synthesis of Ion-exchangers

There is a variety of methods for immobilising ligand-forming compounds to surfaces [Hermanson, G. T., Mallia, A. K. & Smith, P. K., (Eds.), *Immobilisation Affinity Ligand Techniques*, Academic Press, INC, 1992.] of which many are applicable for our purpose. In the following, we shall describe the methods we have adopted for preparing the new series of weak cation-exchangers (based on carboxylic acids) to serve as examples. As base matrix, we have used Sepharose 6 Fast Flow (Amersham Pharmacia Biotech, Uppsala, Sweden) which is beaded agarose that has been cross-linked with epichlorohydrin.

1.1. Activation of Sepharose 6 Fast Flow with Allyl Glycidyl Ether

Activation is performed by reacting allylglycidyl ether with Sepharose 6 Fast Flow under alkaline conditions, essentially as described in WO 97/29825 (Amersham Pharmacia Biotech AB). In a suitable reaction vessel, 80 g of Sepharose 6 Fast Flow was mixed with 0.5 g of $NaBH_4$, 13 g of $Na_2SO_4$ and 40 mL of 50% (w/w) aqueous solution of NaOH. The mixture was stirred for 1 hour at 50° C. and 100 mL of allylglycidyl ether was added. The suspension was stirred for an additional 18 h at 50° C. The mixture was filtered and the gel washed successively with 500 mL of distilled water, 500 mL of ethanol, 200 mL of distilled water, 200 mL of 0.2 M acetic acid, and finally with 500 mL of distilled water.

Analysis by titration resulted in a degree of substitution of 0.3 mmol of allyl groups/mL of gel. In the following, the allyl-derivatised Sepharose 6 Fast Flow will be referred to as Product I.

1.2. Introduction of Carboxyl Groups (Alternative 1)

Introduction of carboxyl groups can be achieved by coupling reactive nucleophiles containing carboxyl groups (e.g. mercaptopropionic acid) to Product I. It can also be achieved by conventional carboxy-methylation of Sepharose 6 Fast Flow with chloroacetic acid under alkaline conditions. The resulting product can be used as a cation-exchanger as such or serve as an intermediate for synthesizing other cation-exchangers via an amide linkage. The procedure described below provides an example for coupling mercaptopropionic acid to Product I (allyl-derivatised Sepharose 6 Fast Flow)

1.2.1. Activation of Product I (Allylated-sepharose 6 Fast Flow).

In a typical procedure, bromine water was added to a stirred suspension of 100 mL of Product I, 4 g of sodium acetate and 100 mL of distilled water, until a persistent yellow colour was obtained. Reduction of excess bromine was achieved by adding sodium formate to the suspension until the faint yellow colour disappeared. The reaction mixture was filtered and the allyl-derivatised gel washed with 500 mL of distilled water.

1.2.2. Coupling of Mercaptoropionic Acid to Activated Product I.

The activated gel (Product I) was transferred to a reaction vessel followed by a mixture of 17.5 mL of mercaptopropionic acid (6 equivalents per allyl group) and 50 mL of 4 M NaCl. The pH of the mixture was adjusted to pH 11.5 with 50% (w/w) aqueous NaOH before it was added to the activated gel. The suspension was stirred for 18 hours at 50° C. and then filtered. The gel was washed with 500 mL of distilled water and its content of carboxyl groups was determined by titration. This gave a degree of substitution of about 0.29 mmol COOH group/mL of gel. This product will be referred to as Product II.

1.3. Introduction of Carboxyl Groups (Alternative 2)

This provides an alternative method for coupling ligand-forming compounds (containing both amino and carboxyl functions) to a solid support via an amide bond. The procedure involves two steps and is described below.

1.3.1. Activation of Mercaptopropionic Acid-Sepharose 6 Fast Flow (Product II) with N-hydroxysuccinimide.

100 mL of mercaptopropionic acid-Sepharose 6 Fast Flow (Product II) were washed successively with 300 mL of 1 M NaCl, 500 mL of 0.1 M HCl, 500 mL 50% aqueous acetone and 500 mL of acetone. The gel was allowed to settle and the supernatant siphoned off. The gel was then quantitatively transferred to a reaction vessel followed by a solution of 15.2 g of N-hydroxysuccinimide in 80 mL of acetone and another solution of 29.9 g of dicyclohexylcarbodiimide in 80 mL of acetone. The slurry was stirred for 18 hours at 30° C. The mixture was filtered and the gel washed (by gravity flow) with 10 portions of 150 mL of isopropanol during a period of about 8 hours.

The extent of activation of Product II was approximately 75%, as estimated by reaction with $NH_4OH$. The product obtained here (i.e. NHS-activated mercaptopropionic acid-Sepharose 6 Fast Flow) will be referred to as Product III.

1.3.2. Coupling of Thienyl Serine (Ligand 11) to Product III.

The procedure outlined here provides an example of a general method for coupling ligand-forming compounds via an amide linkage. A solution of thienyl serine (2 g in 8 mL of distilled water) was mixed with 8 mL of 1M $NaHCO_3$ and 10 mL of ethanol and the pH adjusted to pH 8.5 by careful addition of 50% aqueous NaOH. 25 mL of Product III (NHS-activated mercaptopropionic acid-Sepharose 6 Fast Flow) was washed quickly with 50 mL of ice-cold 1 mM solution of HCl on a sintered glass funnel. The gel was then transferred to an Erlenmeyer flask and the solution of thienyl serine was added to it. The reaction mixture was then shaken at moderate speed for 18 h at room temperature.

The reaction mixture was filtered and the gel washed sequentially with 100 mL of distilled water, 50 mL of ethanol, 50 mL of 0.25 M aqueous ethanolamine, 50 mL of distilled water, 50 mL of 1M NaCl, and finally with 50 mL of distilled water. The efficiency of the coupling of thienyl serine was determined to be about 70% by elementary sulphur analysis which corresponds to a degree of substitution of 0.15 mmol of thienyl serine per mL of gel. Most of the cation-exchangers used for desalting were prepared by this method.

2. Chromatography

In this investigation, two purified proteins, namely human immunoglobulin (IgG) and bovine serum albumin (BSA) were used to characterise the new series of cation-exchangers for desalting with respect to two important parameters. These were breakthrough capacity ($Qb_{10\%}$) at high salt conditions and recovery of proteins applied to the invented cation-exchangers at low salt conditions. IgG was bound at pH 4.5 using a mobile phase containing, in addition to the buffer components, a relatively high concentration of salt (0.25 M). IgG was then eluted with 0.10 M phosphate buffer adjusted to pH 7.0. BSA was bound at pH 4.0 also at a high salt condition (see buffer solutions below) and eluted by raising the pH to 7.0, as in the case of IgG. The procedures used to determine breakthrough capacities for the new series of ligands for desalting, and the recovery of proteins bound to them, are outlined below.

2.1. Breakthrough Capacity ($Qb_{10\%}$) at "High Salt" Conditions

One of the main criteria for a cation-exchange ligand suitable for a desalting procedure is its binding capacity for proteins in the presence of relatively high concentrations of salt (e.g. 0.25 M NaCl) compared to a reference ion-exchanger that is operated under identical conditions. This is determined using the method of frontal analysis as described below.

2.1.1. Experimental.

Buffer solutions

Buffer 1: 20 mM sodium acetate, 0.25 M sodium chloride, pH 4.0

Buffer 2: 20 mM sodium acetate, 0.25 M sodium chloride, pH 4.5

Buffer 3: 100 mM sodium phosphate, pH 7.0 (for elution of BSA and IgG)

Protein solutions

1. BSA: 4 mg/mL in Buffer 1
2. IgG: 4 mg/mL in Buffer 2

All buffers and protein solutions were filtered through a 0.45 μm Millipore Millex HA filter before use.

Chromatography System

All experiments were performed at room temperature using Äkta Explorer 100 chromatography system equipped with Unicom 3.1 software. Samples were applied to the columns via a 150 mL superloop. A flow rate of 1 mL/min (ca. 300 cm/h) was used throughout. The effluents were monitored continuously by absorbance measurements at 280 nm using a 10 mm flow cell.

2.1.2 Frontal Analysis.

Each prototype cation-exchanger was packed in an HR5/5 column (packed bed volume=1 mL, Amersham Pharmacia Biotech AB)) and equilibrated with a buffer of appropriate pH and salt concentration. The void volume of the system was determined by applying a solution of a suitable protein to the column under non-binding conditions. The time it takes for the $A_{280}$ of the effluent to reach 10% of the $A_{280}$ of the applied protein solution is taken as the void volume of the system (expressed in minutes).

To a column equilibrated with an appropriate buffer (Buffer 1 or 2) the sample protein dissolved in the appropriate equilibration buffer (see above) was continuously fed (e.g. via a 150 mL super loop) at a flow rate of 1 mL/min (i.e. ca. 300 cm/h). The application of the sample was continued until the $A_{280}$ of the effluent reached a level of 10% of the $A_{280}$ of the sample applied to the column. On the basis of data so obtained the breakthrough capacity of the packed gel, at a level of 10% of the concentration of the protein applied to it ($Qb_{10\%}$), can be calculated. The results so obtained have formed the basis for screening a large number of candidates for desalting and will be presented below for two proteins, viz. bovine serum albumin (BSA) and human immunoglobulin (IgG).

Evaluation.

The breakthrough at a level of 10% of the absorbance maximum ($Qb_{10\%}$) was calculated using the following relationship:

$$Qb_{10\%} = (T_{R10\%} - T_{RD}) \times C/V_C$$

$T_{R10\%}$=retention time (min) at 10% of the absorbance maximum $T_{RD}$=void volume of the system (in min)

C=concentration of the feed protein (4 mg/mL)

$V_C$=packed bed volume (mL) of the column 2.2. Recovery of Proteins Bound to "High Salt" Cation-exchange Ligands The cation-exchange ligands are also screened with respect to the recovery of proteins bound to them at low salt conditions. This is an additional and important criterion for choosing the right kinds of ligands that combine relatively high adsorption capacities at high salt conditions with high or quantitative recoveries at low salt conditions of proteins applied to them. The recovery was determined as outlined below.

2.2.1. Experimental.

Details concerning type of column, packed bed volume, buffers, protein solutions, flow rate and type of apparatus used are outlined under sections 2.1.1. and 2.1.2. For BSA, the column was equilibrated with Buffer 1 and the bound protein eluted with Buffer 3 and for IgG, the column was equilibrated with Buffer 2 and the bound protein eluted with Buffer 3.

To a column equilibrated with the appropriate buffer (Buffer 1 or 2) was applied a solution of the protein (BSA or IgG) from a 50 mL super loop until an amount corresponding to 30% of its breakthrough capacity was applied. The column was then washed with 2 bed volumes of the equilibration buffer and the bound protein was eluted with the appropriate de-sorption buffer (Buffer 3). The eluted protein is collected quantitatively in a 20 mL volumetric flask and its volume and absorbance at 280 nm (for BSA and IgG) was measured accurately. On the basis of the total absorbance in each eluted sample, the amount of protein in the eluates was calculated using an appropriate calibration curve (see below).

2.2.2. Evaluation.

Standard solutions for each protein were prepared covering the concentration range of 0–10 mg/mL in the column equilibration buffer. The $A_{280}$ (BSA or IgG) of the series of dilutions were measured and a calibration curve was prepared with the protein concentration (mg/mL) on the x-axis and the absorbance on the y-axis. The linear equations and regression coefficients of each of the calibration curves were calculated. On the basis of these standard curves, the concentration (in mg/mL) of protein in the eluted sample was calculated by measuring the $A_{280}$ of said sample using the following relationship:

$$C_S = \frac{A}{\varepsilon \cdot b}$$

$C_S$=concentration of protein in the eluted sample (mg/mL)
A=absorbance (at $A_{280}$)
$\varepsilon$=molar absorptivity at a specific wavelength ($M^{-1}$ $cm^{-1}$)
b=cell path length (cm)

The recovery of the bound protein is then calculated using the following relationship:

$$\text{Recovery, }\% = \frac{C_S \cdot V_S}{C_L \cdot V_L}$$

$V_S$=volume of the eluted protein sample (mL)
$C_L$=concentration of the protein in the applied sample (mg/mL)
$V_L$=volume of the applied sample (mL)

Results

1. Breakthrough Capacity at High Salt Conditions

The results obtained for breakthrough capacities and recoveries for a series of representative desalting cation-exchange ligands are summarised in Table 1. The examples shown in Table 1 illustrate some specific properties of the various ligands and should not be interpreted as limitations on the scope of this invention. The degree of ligand substitution on the majority of these new cation-exchangers was ca. 0.18–0.20 mmol/mL of packed gel. A few exchangers had as much as 0.27 mmol/mL of packed gel. As a reference cation-exchanger, the commercially available SP Sepharose 6 Fast Flow was used whose ligand concentration is in the same range as the new series of cation-exchangers (i.e. 0.18–0.25 mmol/mL of packed gel). The results indicate the following trends:

1. The new desalting cation-exchange ligands have a much higher $Qb_{10\%}$ for both proteins compared to the reference cation-exchanger SP Sepharose Fast Flow. The $Qb_{10\%}$ values for SP Sepharose Fast Flow were 2.6 mg/mL and 0.8 mg/mL for BSA and IgG, respectively.
2. Ligand 13 gave the highest value for BSA (57 mg/mL) and ligand 1 for IgG (33 mg/mL). These values correspond to an increase of breakthrough capacity corresponding to 2192% and 4125% of BSA and IgG, respectively, on the above two ligands (13 and 1) relative to the reference cation-exchanger (SP Sepharose 6 Fast Flow).
3. Of the 17 ligands presented below, all showed significantly higher $Qb_{10\%}$ for both proteins compared to the reference cation-exchanger. This indicates that these ligands can form the basis for the construction of future desalting ligands.
4. Some ligands show relatively low $Qb_{10\%}$ values for IgG (lower than 8 mg/mL) but high $Qb_{10\%}$ values for BSA (e.g. ligands 11, 12,14, 15, 16 and 17). These results can thus serve as guidance for the construction "specific" types of desalting cation-exchangers in the future.

2. Recovery of Proteins Bound to "High Salt" Cation-exchange Ligands

The recovery data for BSA are complete while those for IgG are determined for about 50% of the ligands. The results obtained indicate:

1. All the ligands give a recovery of BSA better than 79%.
2. Ligand 1 is the most optimal ligand in this respect exhibiting a recovery for BSA and IgG of 93% and 88%, respectively.
3. The results also show that step-wise elution with pH results in high yields.

Structure of Ligands.

Cation-exchange ligands (Table 1) were created by reacting
(a) the ligand-forming compounds 1–13, 15 and 17 with the NHS-activated form of Product II or
(b) the ligand-forming compounds 14 and 16 with the bromine activated form of Product I.

Variant (a) implies that the ligand-forming compound was linked to the matrix via an amide group. Variant (b) means linkage via a thioether.

$Q_b$ stands for the breakthrough capacity at 10% breakthrough in the flow through. mL refers mL of the gel.

TABLE 1

Cation-exchange ligands used for ion-exchange desalting.

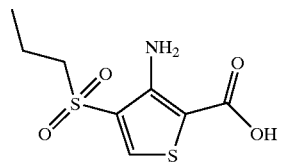

Ligand 1. $Q_b$ BSA = 50 mg/mL, $Q_b$ IgG = 33 mg/mL, Recovery BSA = 93%, Recovery IgG = 88%.

TABLE 1-continued

Cation-exchange ligands used for ion-exchange desalting.

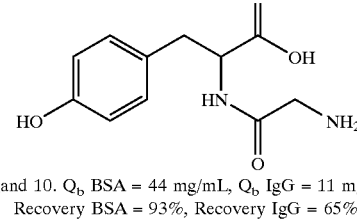

Ligand 2. $Q_b$ BSA = 44 mg/mL, $Q_b$ IgG = 20 mg/mL, Recovery BSA = 86%, Recovery IgG = 68%.

Ligand 3. $Q_b$ BSA = 42 mg/mL, $Q_b$ IgG = 27 mg/mL, Recovery BSA = 93%, Recovery IgG = 79%.

Ligand 4. $Q_b$ BSA = 44 mg/mL, $Q_b$ IgG = 24 mg/mL, Recovery BSA = 91%, Recovery IgG = not determined.

Ligand 5. $Q_b$ BSA = 41 mg/mL, $Q_b$ IgG = 27 mg/mL, Recovery BSA = 93%, Recovery IgG = not determined.

Ligand 6. $Q_b$ BSA 50 mg/mL, $Q_b$ IgG = 22 mg/mL, Recovery BSA = 93%, Recovery IgG = 75%.

Ligand 7. $Q_b$ BSA = 40 mg/mL, $Q_b$ IgG = 23 mg/mL, Recovery BSA = 93%, Recovery IgG = 76%.

Ligand 8. $Q_b$ BSA = 38 mg/mL, $Q_b$ IgG = 23 mg/mL, Recovery BSA = 93%, Recovery IgG = 86%.

Ligand 9. $Q_b$ BSA = 43 mg/mL, $Q_b$ IgG = 14 mg/mL,

TABLE 1-continued

Cation-exchange ligands used for ion-exchange desalting.

Recovery BSA = 79%. Recovery IgG = 66%.

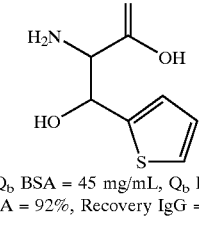

Ligand 10. $Q_b$ BSA = 44 mg/mL, $Q_b$ IgG = 11 mg/mL, Recovery BSA = 93%, Recovery IgG = 65%.

Ligand 11. $Q_b$ BSA = 45 mg/mL, $Q_b$ IgG = 5 mg/mL, Recovery BSA = 92%, Recovery IgG = not determined.

Ligand 12. $Q_b$ BSA = 49 mg/mL, $Q_b$ IgG = 6 mg/mL, Recovery BSA = 92%, Recovery IgG = not determined.

Ligand 13. $Q_b$ BSA = 57 mg/mL, $Q_b$ IgG = 10 mg/mL, Recovery BSA = 93%, Recovery IgG = not determined.

Ligand 14. $Q_b$ BSA = 51 mg/mL, $Q_b$ IgG = 4 mg/mL, Recovery BSA = 92%, Recovery IgG = not determined.

Ligand 15. $Q_b$ BSA = 46 mg/mL, $Q_b$ IgG = 3 mg/mL, Recovery BSA = 87%, Recovery IgG = not determined.

Ligand 16. $Q_b$ BSA = 51 mg/mL, $Q_b$ IgG = 4 mg/mL, Recovery BSA = 91%, Recovery IgG = not determined.

TABLE 1-continued

Cation-exchange ligands used for ion-exchange desalting.

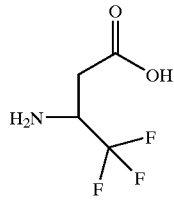

Ligand 17. $Q_b$ BSA = 37 mg/mL, $Q_b$ IgG = 7 mg/mL, Recovery BSA = 93%, Recovery IgG = not determined.

What is claimed is:

1. A method for desalting an aqueous liquid containing a charged substance comprising the steps of:
   (i) contacting liquid (I) with an ion-exchanger (1) under conditions permitting binding between the ion-exchanger and the substance, said ion exchanger comprising a base matrix carrying an ion-exchange ligand (Ligand 1) that has the opposite charge compared to the substance,
   (ii) desorbing said substance from said ion-exchanger by the use of a liquid (liquid (II)),
   wherein
   (A) ion-exchanger (1) is selected among ion-exchangers that:
      (a) are capable of binding the substance of interest in an aqueous reference liquid at an ionic strength corresponding to 0.1 M NaCl; and
      (b) permit a breakthrough capacity at the pH provided by liquid (I) which is more than 2 mg/ml of gel (sedimented), at a breakthrough of 10% and a linear flow velocity of 300 cm/h;
   and
   (B) step (ii) comprises that the pH of liquid (II) is adjusted to a pH value that means that the charge difference between the substance and the ligand and/or the ion-exchanger is lowered.

2. The method of claim 1, wherein the substance is bio-organic and amphoteric with two or more charged groups and a molecular weight above 1,000 Dalton.

3. The method of claim 1, wherein the adjustment leads to zero charge on the substance and/or on Ligand 1/ion-exchanger or to a charge of the same kind for both of them (either negative or positive).

4. The method of claim 1, wherein Ligand 1 is a cation-exchange ligand a mixed mode cation-exchange ligand.

5. The method of claim 1, wherein Ligand 1 is an anion-exchange ligand a mixed mode anion-exchange ligand.

6. The method of claim 1, wherein Ligand 1 have a pH-independent charge or can be decharged by a pH-switch.

7. The method of claim 1, wherein the ion-exchanger is stochastic and comprises also a second ligand (Ligand 2).

8. The method of claim 7, wherein Ligand 2 at the condition provided by liquid (I) is (a) uncharged but chargeable by a pH switch, or (b) uncharged and not chargeable, or (c) charged by a pH-independent charge, or (d) charged by a pH-dependent charge.

9. The method of claim 7, wherein Ligand 2 is a mixed mode ligand.

10. The method of claim 1, wherein
    (a) in liquid (I) the ionic strength is at least the ionic strength corresponding to 0.1 M NaCl, and
    (b) in liquid (II) the ionic strength contribution from non-buffering components and their associated counter-ions is at most 10% of the ionic strength of liquid (I), with preference for said ionic strength contribution in liquid (II) being at most the ionic strength of a 0.01 M NaCl.

11. The method of claim 1, wherein the buffer used in step (ii) is volatile and is evaporated in a step preceding step (ii).

12. The method of claim 1, wherein the substance to be desalted is present in liquid (II) after step (ii) in a concentration that is at least 10 times the concentration in liquid (I).

13. The method of claim 1, wherein
    (a) the substance is present in liquid (I) together with other substances comprising a structure selected amongst peptide structure nucleic acid structure, carbohydrate structure, lipid structure, steroid structure, amino acid structure, nucleotide structure, and
    (b) the total amount of these other substances are reduced with at least a factor 10 after step (ii) in a fraction of liquid (II) that also contains the substance to be desalted.

14. The method of claim 1, wherein liquid (I) consists essentially of the substance to be desalted, salts and an aqueous solvent.

15. The method of claim 1, wherein liquid II containing the substance after step (ii) is further processed to a dry form, either directly or indirectly.

16. The method of claim 1, wherein the method is a part of an analytical procedure or of a process for manufacturing a composition containing the desalted substance or a derivative thereof,
    said composition being intended to be used as a pharmaceutical or within the food industry.

17. The method of claim 1, wherein the ion exchanger has been selected amongst those ion exchangers that permit a maximal breakthrough capacity in the pH interval 2–12 for the substance which is ≧100% of the breakthrough capacity of the substance for the corresponding ion-exchanger in which the ion-exchange ligands are
    (i) sulphopropyl groups when the substance has a positive charge (reference ion-exchanger 2a), and
    (ii) quaternary ammonium groups when the substance has a negative charge (reference ion-exchanger 2b); the measurements being performed under essentially the same conditions for ion-exchanger (I) and (2a) and for ion-exchanger (I) and (2b).

* * * * *